US012186073B2

(12) United States Patent
Babic

(10) Patent No.: US 12,186,073 B2
(45) Date of Patent: Jan. 7, 2025

(54) DIVIDER FOR DETERMINING THE GOLDEN SECTION OF EYEBROWS

(71) Applicant: PHIACADEMY DOO BEOGRAD-VOZDOVAC, Beograd (RS)

(72) Inventor: Branko Babic, Beograd (RS)

(73) Assignee: PHIACADEMY DOO BEOGRAD-VOZDOVAC, Beograd (RS)

(*) Notice: Subject to any disclaimer, the term of this patent is extended or adjusted under 35 U.S.C. 154(b) by 349 days.

(21) Appl. No.: 17/626,103

(22) PCT Filed: Aug. 23, 2019

(86) PCT No.: PCT/RS2019/050003
§ 371 (c)(1),
(2) Date: Jan. 10, 2022

(87) PCT Pub. No.: WO2021/006754
PCT Pub. Date: Jan. 14, 2021

(65) Prior Publication Data
US 2022/0313117 A1    Oct. 6, 2022

(30) Foreign Application Priority Data
Jul. 11, 2019  (RS) .............................. MP-2019/0053

(51) Int. Cl.
*A45D 40/30*    (2006.01)
*A61B 5/107*    (2006.01)

(52) U.S. Cl.
CPC ............ *A61B 5/1077* (2013.01); *A45D 40/30* (2013.01)

(58) Field of Classification Search
CPC .... A45D 40/30; A45D 44/002; A61B 5/1077; A61B 5/107
See application file for complete search history.

(56) References Cited

U.S. PATENT DOCUMENTS 2,487,451 A * 11/1949 Kurmer .................... G01B 3/02
33/558.02
3,300,864 A * 1/1967 Lesslie ................. G06V 40/171
132/216
(Continued)

FOREIGN PATENT DOCUMENTS

CN          2652331 Y  * 11/2004
CN        202408907 U     9/2012
(Continued)

OTHER PUBLICATIONS

Machine Translation Li (Year: 2017).*
Gao Machine Translation (Year: 2012).*

*Primary Examiner* — Rachel R Steitz
*Assistant Examiner* — Brianne E Kalach
(74) *Attorney, Agent, or Firm* — The Watson IP Group, PLC; Jovan N. Jovanovic

(57) ABSTRACT

The present invention solves the problem of implementation of the divider for determining the golden section of eyebrow in relation to face, which would have an improved construction compared to the dividers known in the art and would be easier to handle, and owing to the smaller number of visible structural elements would also have an innovative, improved design. Divider for determining the golden section of eyebrows according to the invention comprises two arms (1), which are pivotally connected to each other via a serrated gear, with each arm (1) having the longer part (b) and the shorter part (a) whose length ratios are equal to the golden ratio, i.e. 1.618, while the ratio of the distance (c) between the longer parts (b) of the arms and the distance (d) between the shorter parts (a) of the arms are also equal to the golden ratio, i.e. 1.618.

5 Claims, 5 Drawing Sheets

(56) References Cited

U.S. PATENT DOCUMENTS

Figure 1:
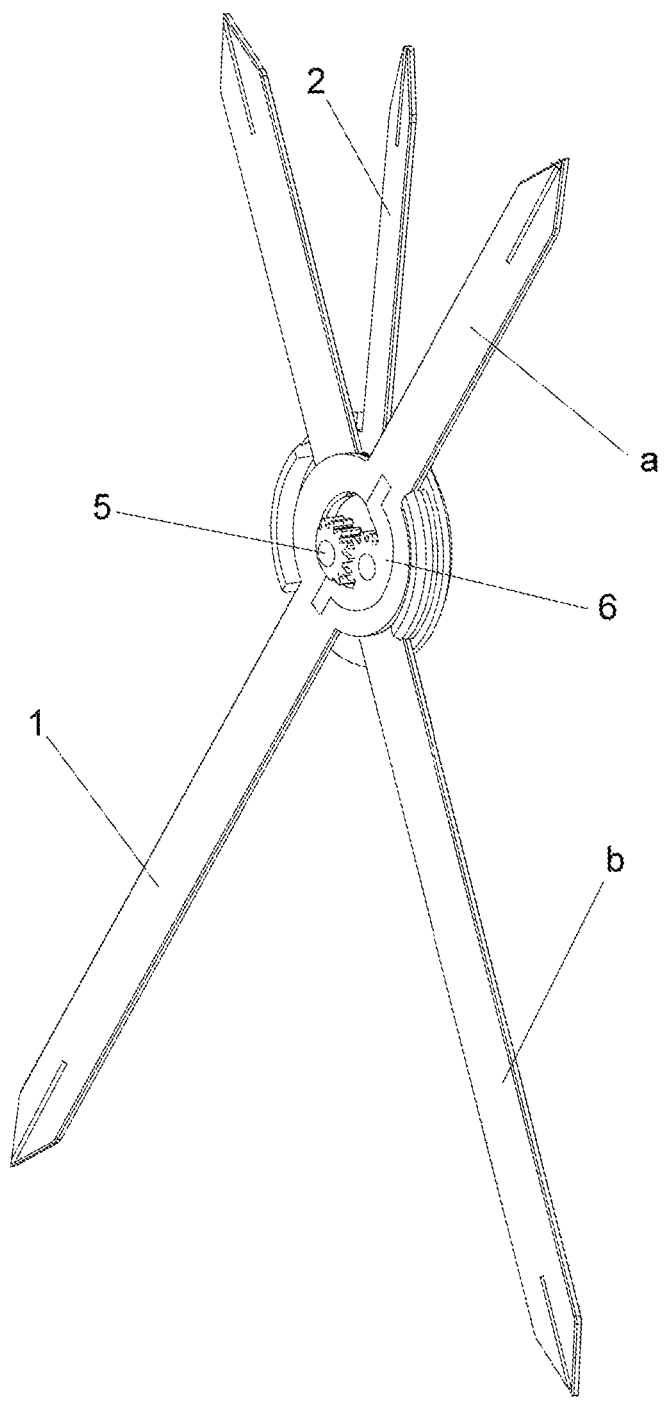

| 7,895,765 | B2 * | 3/2011 | Plain | ............ | A45D 40/30 |
|---|---|---|---|---|---|
| | | | | | 33/512 |
| 2010/0229886 | A1 * | 9/2010 | Plain | ............ | A45D 40/30 |
| | | | | | 132/319 |

FOREIGN PATENT DOCUMENTS

| CN | 102972969 B | * | 4/2015 |
|---|---|---|---|
| CN | 205947405 U | * | 2/2017 |
| CN | 207734164 U | | 8/2018 |

* cited by examiner

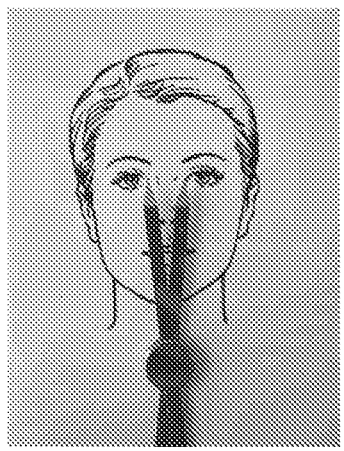
Fig. 5.1
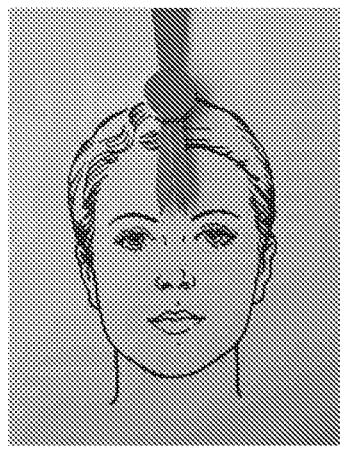
Fig. 5.2
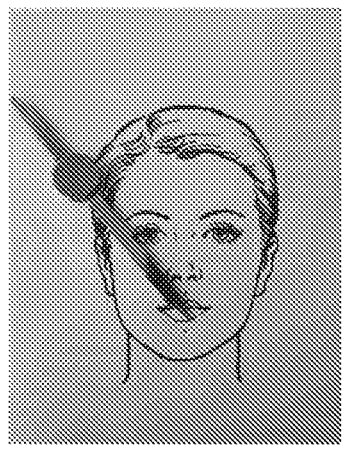
Fig. 5.3
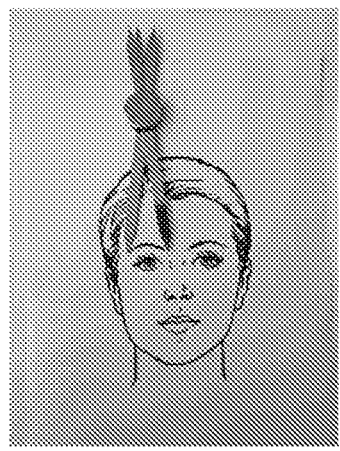
Fig. 5.4
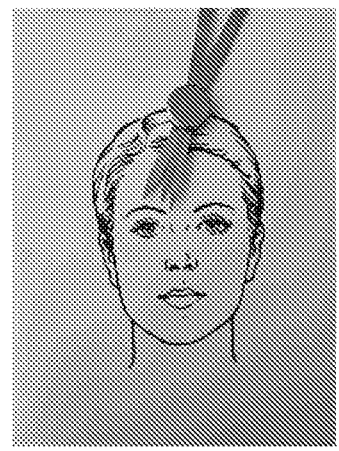
Fig. 5.5
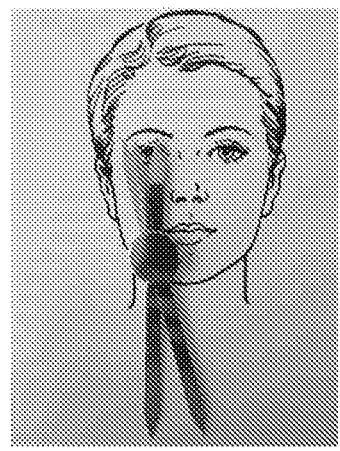
Fig. 5.6
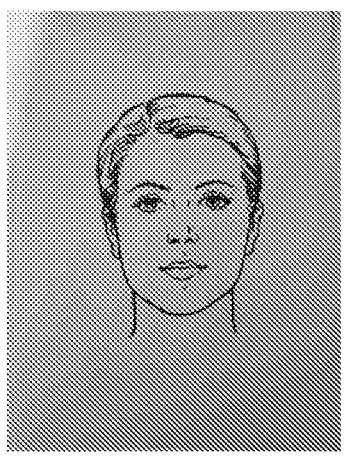
Fig. 5.7

DIVIDER FOR DETERMINING THE GOLDEN SECTION OF EYEBROWS

TECHNICAL FIELD

The present application relates to a new technical solution of a divider for determining the golden section of eyebrows in relation to the face, which is applied to measure and precisely determine the five key points on the face before drawing eyebrows, in order to achieve the most natural possible appearance of eyebrows penned in such a manner. Accordingly, the present invention relates to the field of cosmetics, and in particular to cosmetic procedures and accessories.

TECHNICAL PROBLEM

The present invention solves the problem of technical design of a divider for determining the golden section of the eyebrows in relation to the face, which would have an improved construction compared to the dividers known in the art, which have been used for the same purposes so far. Such a divider should also be easier to handle and, thanks to fewer visible structural elements, should be distinguished by its innovative, advanced design.

STATE-OF-THE-ART

Divider according to the invention is indented to be used in microblading, that is, in Japanese eyebrow drawing. This procedure is performed using specially designed small blades, the shape of which corresponds to the shape of an eyebrow hair, by which the pigment of the desired color is introduced below the basal membrane that divides the epidermis from the dermis. Eyebrows drawn like this are semi-permanent and persist for a period of 3 to 5 years, with repeated treatments once every six months to a year. The aim of this procedure is to make the drawn eyebrows look as natural as possible, since it can be achieved by the fact that the drawn hairs have different thicknesses, lengths and densities, as is the case with natural eyebrows.

In addition, what is particularly significant about eyebrows is their shape, especially given their prominent position on the face. The shape of the eyebrows is dictated by the facial features, namely the nasal bone, the forehead and the arcade, but of particular importance for their most natural appearance is the use of the golden section.

In mathematics, two lengths are considered to be in the golden ratio if the ratio between the two lengths is equal to the ratio of the sum of these lengths compared to the length of the longer one, which is mathematically expressed by the following relation:

$$\frac{B}{A} = \frac{A+B}{B} = 1{,}618,$$

on condition that B>A>0.

This proportion, denoted by the Greek letter φ (read: fi), evokes a special aesthetic experience, hence its other name, "Divine Section". The golden section also occurs in space (where it characterizes the shape of certain galaxies), and in nature, including plants (for example, in the spiral arrangement of leaves along a tree or stem), animals (e.g., the spiral shape of the snail's shell) and humans, and especially parts of the human body. Its application in architecture and art is well known ever since the time of ancient Greece, and has continued through the Renaissance until the present day.

Today, one of the current areas of application of the gold section is microblanding (also known as Japanese eyebrow drawing), where the gold section is used to determine the points on the face that define the contour of the eyebrows that will be drawn using this technique. Special tools have been designed for this purpose, which are generally in the shape of a divider.

In the previous period, the applicant had developed their own solution of a divider for determining the golden section of eyebrows in relation to the face, which had been successfully marketed under the commercial name PhiBrows® Divider. The construction solution and the method of use of this divider in the state-of-the-art may be seen at the following link: https://www.youtube.com/watch?v=eeYEYUrDFAI Although the presented divider still largely satisfies the needs of the user, the applicant considered that there was room for further improvement of its construction, with the aim of achieving a simpler, faster and cheaper production than the divider known in the art. In addition, it is desirable that the new divider solution be lighter, more precise and more reliable to operate, as well as to have even better ergonomic features compared to known dividers used for the same purposes so far. Also, the need to further enhance the aesthetic appearance of the divider should not be neglected. All of these goals were fully accomplished by a divider for determining the golden cross of the eyebrows in relation to the face that constitutes the invention.

SUMMARY OF THE INVENTION

The technical problem defined above has been solved by a divider for determining the gold section of eyebrows according to the invention, which comprises two arms, characterized in the fact that said two arms are connected to each other via a gear, with each arm having a longer part and a shorter part, whose relation in length is equal to the golden ratio, i.e. 1.618, and the ratio of the distance between the longer parts of the arms and the distance between the shorter parts of the arms are also equal to the golden ratio, that is, 1.618.

This means that the lengths of the divider's arms are in the golden ratio. Moving the arms in any direction, the distances that arise between the arms are also in golden ratio. This feature of the divider is used to convey golden ratios to the face/eyebrows in order to draw appropriate points, which are necessary to define the contour of the eyebrows that will look quite natural and harmonious.

Said serrated gear is formed by reciprocating the serrated segment of the first annular insert and the serrated segment of the second annular insert, with one arm fixedly mounted on each of the annular inserts.

In addition, said gear train is mounted through the shafts in a housing, to which the middle arm is fixed, which has an extended part to which its body extends, which viewed from above, has a rectangular shape, while its opposite end has the shape of an equilateral triangle. In contrast to this fixed middle arm, each of the movable arms has the form of a flat ring from whose opposite sides extend the shorter part of the arm and the longer part of the arm, at which the parts of the arms viewed from above have a rectangular shape, while their ends have the shape of the equilateral triangle.

Further, the first and the second annular inserts are in the form of a flat ring on one side of which, along the circular arched of the rim of the central opening of the annular insert, is a "C"-shaped arched segment. In addition, from the rim of the central opening of the annular insert extends a serrated segment in which a through opening is made in which the shaft is housed, and the height of the serrated segment is greater than the height of the arched segment.

Most preferably, said annular inserts are made of plastic and the other structural elements are made of steel, primarily stainless steel, which has a number of advantages in terms of ease of manufacture and use, but also meets the hygiene requirements for the use of the invention. Of course, this does not preclude the use of other materials having equivalent properties to the foregoing, which is a routine task for a person skilled in the art.

Summing up, it follows that on the one hand, thanks to the improved construction of the divider, its simpler, faster and cheaper production is enabled, while on the other hand, the new divider for determining the golden section of eyebrows in relation to the face is easier, more precise and more reliable to handle and has better ergonomic properties compared to the dividers that are already state-of-the-art. In addition to the technical advantages mentioned, this divider also has a distinct aesthetic properties, since it has less visible structural elements. With all this in mind, it is obvious that the divider for determining the golden section of eyebrow in relation to face is significantly improved compared to the dividers known in the art.

SHORT DESCRIPTION OF THE DRAWINGS

Figure 2:
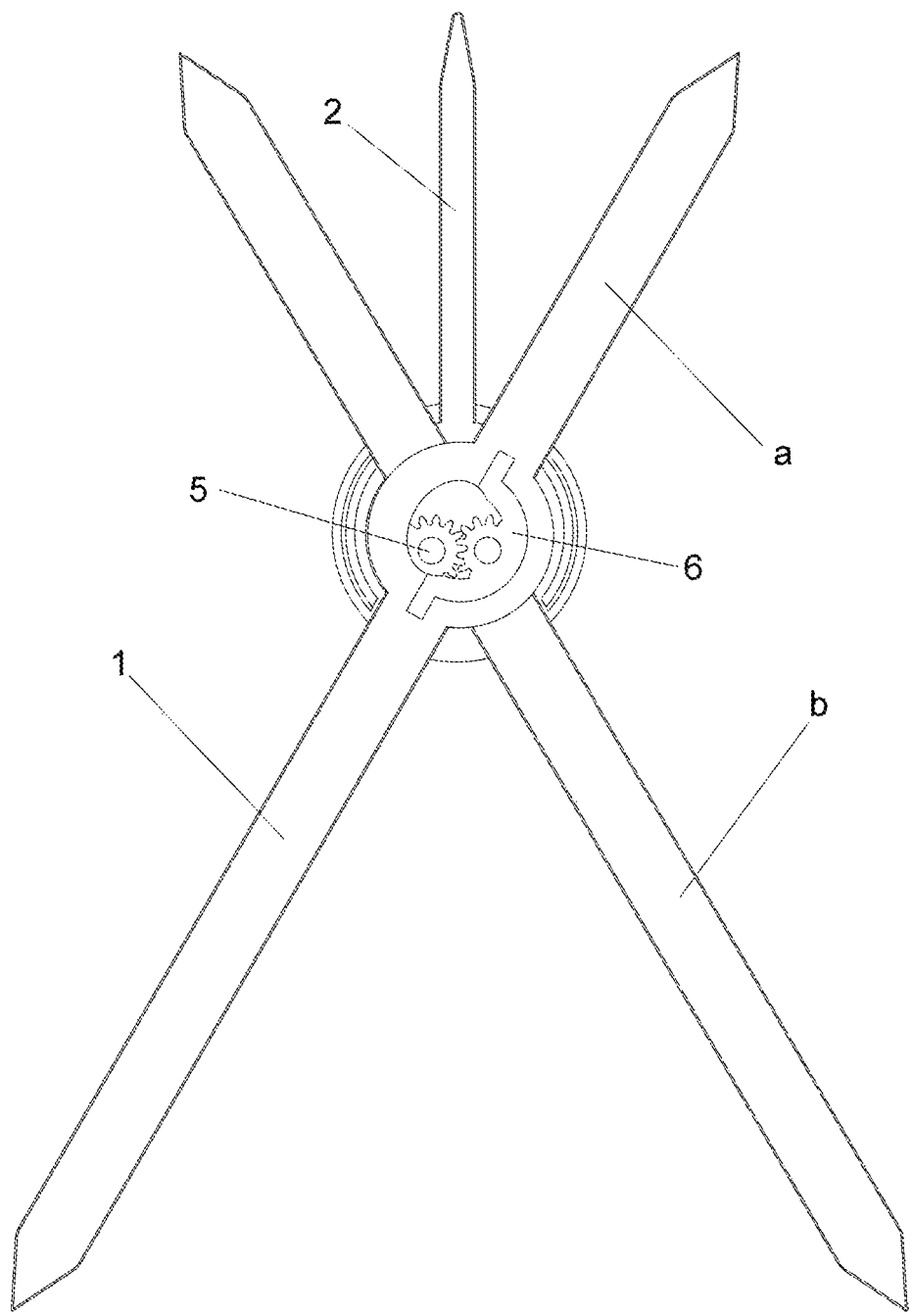
Figure 3:
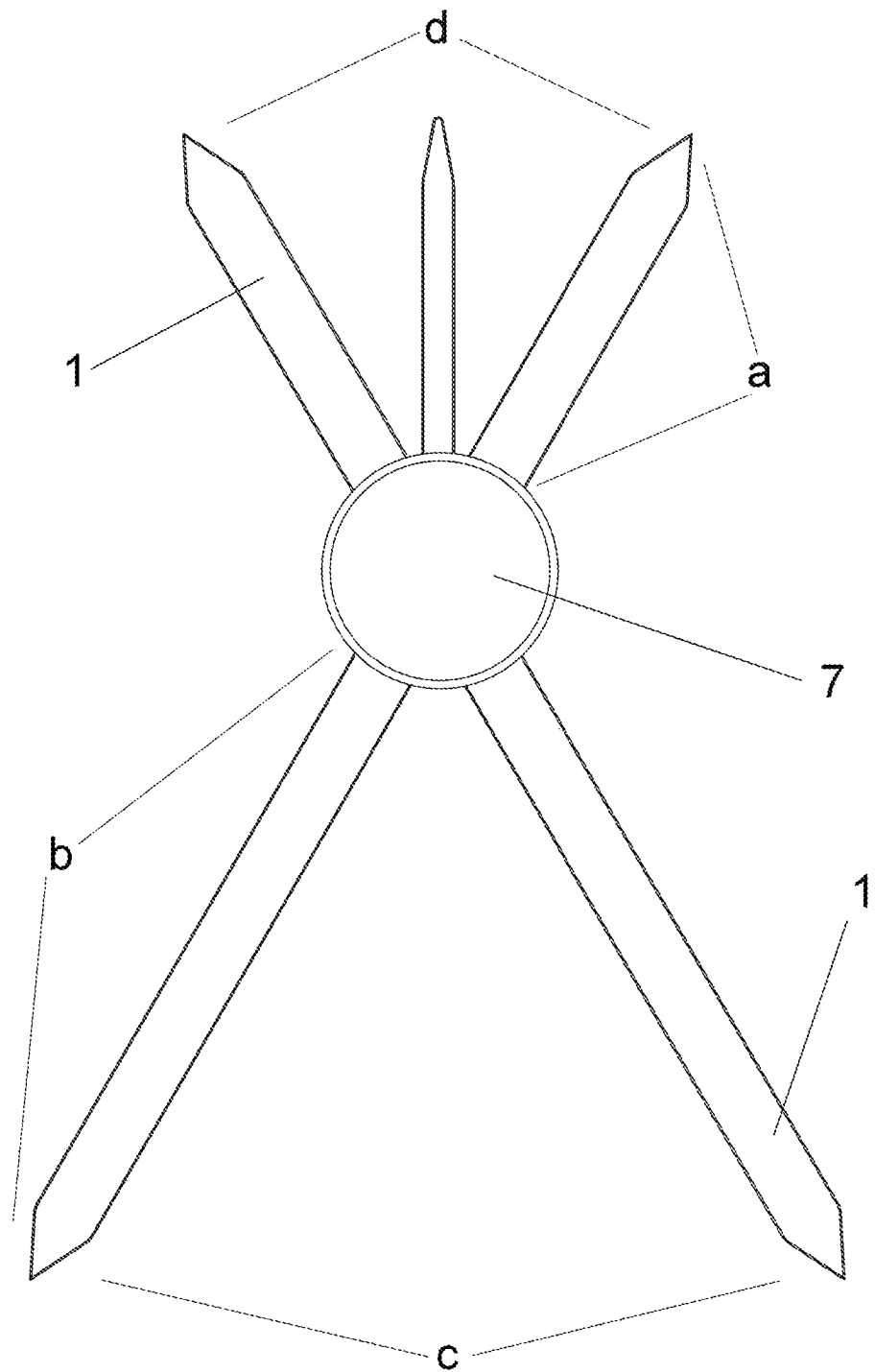
Figure 4:
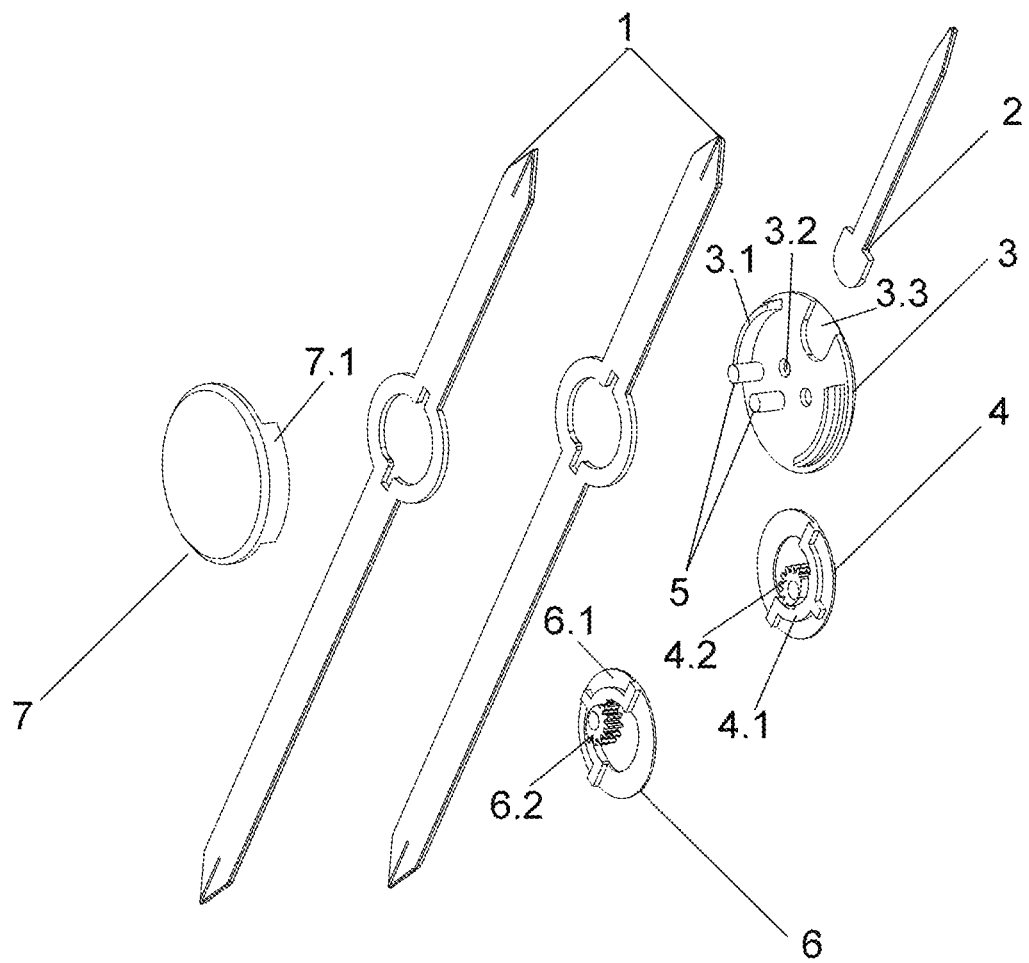

Divider for determining the golden section of eyebrow according to the invention will be described in more detail below, based on one embodiment shown in the Figures. The Figures display the following:

FIG. 1 displays the axonometric layout of the divider according to the invention with the cover removed, FIG. 2 displays the divider according to the invention with the cover removed in horizontal projection, FIG. 3 displays the divider according to the invention in horizontal projection, FIG. 4 displays the axonometric appearance of the disassembled divider according to the invention.

FIGS. 5.1-5.7 display the steps of using a divider according to the invention in microblading.

DETAILED DESCRIPTION OF THE INVENTION

The construction of the divider for determining the golden section of eyebrow according to the invention will be described in detail below. As can be seen in FIG. 4, said divider contains the base 3, which, together with the cover 7, has the function of a housing (as best seen in FIG. 3), otherwise it is a circular plate on the upper side of which to the left and right side there are two arched segments 3.1 in the form of the letter "C". Between these arched segments 3.1, two symmetrically spaced through openings 3.2 are provided to receive cylindrical shafts 5, as well as the notch 3.3, viewed from above, having one part in the form of letter "U" and another part corresponding to the circular arched of the rim of the base 3. Otherwise the depth of the notch 3.3 is less than the thickness of the base 3, while the base of the notch 3.3 is parallel to the circular surfaces of the base 3.

When mounting, first the shafts 5 are mounted in the through openings 3.2 on the base 3. subsequently, an expanded portion of the middle arm 2 is placed in the notch 3.3 on the base 3, the shape of which is complementary to the notch 3.3. The extended part of the middle arm 2 extends its body which, viewed from above, has a rectangular shape, while its opposite end has the shape of an equilateral triangle, also viewed from above. The middle arm 2 is fixed shut to the base 3, for example by welding, such as electro-spot welding.

Thereafter, the first annular insert 4 is inserted between the arched segments 3.1 of base 3, so that its through opening is drawn into one of the shafts 5, in this case the one shown in FIG. 4 to the left. The first annular insert 4 is in the form of a flat ring, on one side of which, along the circular arched of the circumference of its central opening, an arched segment 4.1 is formed in the shape of the letter C. From the ends of the arched segment 4.1, two discharges are provided radially to the outer circumference of the first annular insert 4. From the circumference of the central opening of the first annular insert 4 extends the serrated segment 4. in which said through opening is implemented, which houses shaft 5. The height of the serrated segment 4.2 is greater than the height of the arched segment 4.1.

Then one of the arms 1 is fitted to the first annular insert 4. Each of the arms 1 has the form of a flat ring on the opposite sides of which extend externally the shorter portion a of the arm A and a longer portion of the arm B. Parts of the arms A, B, viewed from above, have a rectangular shape, while their ends have the shape of an equilateral triangle. The ratio between the longer part of the arm B and the shorter part of the arm A is equal to the golden ratio, which can be expressed by the following formula:

$$\frac{b}{a} = \frac{a+b}{b} = 1,618$$

The first arm 1 is immovably attached to the first annular insert 4 in such a way that two radial grooves extending from its central opening engage two corresponding radial outlets extended on the first annular insert 4. Otherwise, the thickness of the arms 1 is such that they can bend slightly under the action of pressure in the axial direction, which is applied when it is necessary to determine more precisely the individual points of the contour of the eyebrow.

Thereafter, the second annular insert 6 is inserted between the arched segments 3.1 and the base 3 so that its passage opening is threaded to the second of the shafts 5. The second annular insert 6 also has the shape of a flat ring, on one side of which, along the circular arched of the circumference of its central opening, the arched segment 6.1 is formed in the shape of the letter "C". From the ends of the arched segment 6.1, two outlets are provided radially to the outer circumference of the second annular insert 6. From the circumference of the central opening of the first annular insert, a serrated segment 6.2 extends in which said passage opening which houses the shaft 5. The height of the serrated segment 6.2 is greater than the height of the arched segment 6.1. When attaching the second annular insert to the second shaft 5, the teeth of its serrated segment 6.2 are geared into the teeth of the serrated segment 4.2 of the first annular insert 4.

Then, the second arm 1, identical to the first arm 1, is attached to the annular insert 6, which connects to the second annular insert 6 in the same way as the first annular insert 4 with the first arm 1. Arms 1 are pivotally interconnected due to their being fixed to the annular inserts 4, 6 which are pivotally connected to each other by their corresponding serrated segments, 4.2, 6.2, as seen in FIGS. 1 and 2. Thanks to the gearing formed in such a manner, not only is the ratio between the longer part b of the arm and the shorter part A of the arm equal to the golden ratio, but also the ratio of the distance C between the longer parts B of the arm and the distance D between the shorter parts A of the arm is equal to the golden ratio, namely:

$$\frac{c}{d} = \frac{c+d}{d} = 1.618$$

Finally, a cover 7 is placed over the assembly formed in such a manner, which is a round plate on the lower side of which two arched segments 7.1 in the shape of the letter "C" extend on its left and right sides. These arched segments 7.1 are adapted to be closely coupled to the corresponding arched segments 3.1 derived on base 3, although their interconnections may be implemented in another way, for example, by gluing, etc. Regardless of the type of their interconnection, cover 7 and base 3 together form a divider housing, intended primarily to protect other structural members from external influences, but whose surface can be used for other purposes, such as informational, marketing or other purposes.

Divider for determining the golden section of eyebrow to the Invention is to be used as follows:

Step 1: Measure the distance between the inner ends of the eyes with the help of the longer sections of the Parts B of the Arms (see FIG. 5.1).

Step 2: The gaps between the eyes and between the eyebrows should be in the golden ratio. Since the distance between the inner ends of the eyes has already been measured by the longer parts b of the arms, then the divider should be turned from the sides of the shorter parts and the arms, and then the face, between the eyebrows, should be marked with lines showing the distance between those shorter parts and the arms. The eyebrows should start from such marked lines so as to be in the golden ratio with the distance between the eyes (see FIG. 5.2).

Step 3: Using the folded divider as a ruler, mark the point on the eyebrows at the same straight line as the outer corner of the eye and the angle of the nose (see FIG. 5.3).

Step 4: With the help of the longer sections B of the divider blades, the length of the eyebrows should be measured by placing the divider arms at two previously drawn points (see FIG. 5.4).

Step 5: Then turn the divider, push one shorter part A of the arms to the beginning of the eyebrow from the upper inner side of the eyebrow and mark the distance between the shorter parts of arms A, i.e. draw the next dot (see FIG. 5.5).

Step 6: Repeat the procedure from the external side of the eyebrow (see FIG. 5.6).

Step 7: Connect the drawn dots. This gives the ideal contour of the eyebrow within which microblading is done (see FIG. 5.7).

The present invention is described by way of of one preferable implementation example, but is not limited to just that one. It is very easy to devise other implementation examples that would not, however, fall outside the scope of the present Invention. Thus, for example, it is desirable that the structural elements of the divider be made of stainless steel, with the exception of annular inserts, which are primarily made of plastic. However, the invention is not limited to the application of these materials, but an expert in the relevant field can perform their replacement with other materials that have the appropriate mechanical and other necessary properties for the successful implementation of the subject-matter Invention.

Likewise, the interconnections of individual structural elements can be realized in a different way. For example, the middle arm 2 and base 3 may be inextricably joined in a different way than welding. Also, the annular segments 4, and 6 and arms 1 can be connected in a different way instead of interconnecting their segments and grooves, provided that such a connection is fixed.

LIST OF PARTS

1 Arms
2 Middle Arm
3 Base
3.1 Arched Segments
3.2 Through Openings
3.3 Notch
4 first Annular Segment
4.1 Arched Segment
4.2 Serrated Segment
5 Shafts
6 second Annular Insert
6.1 Arched Segment
6.2 Serrated Segment
7 Cover
7.1 Arched Segment
a Shorter Part of Arm
b Longer Part of Arm
c Distance between Longer Parts of Arm B
d distance between Shorter Parts of Arm A

The invention claimed is:

1. A divider for determining the gold section of eyebrow, which comprises two arms, characterized in that each arm has a longer part, a shorter part, and a central portion therebetween, wherein the ratio in length of each arm's respective longer part to shorter part is 1.618,
and wherein the central portion of each arm is overlappingly coupled via a gear train, such that the distance (c) between the longer Parts (b) of the arms and the distance (d) between the shorter parts of the arms maintain a ratio equal to 1.618.

2. The divider according to claim 1, wherein the gear train is formed by interconnecting a serrated segment of a first annular insert with a serrated segment of a second annular insert, wherein each of the annular inserts are attached in a fixed manner by one arm.

3. A divider, according to claim 2, characterized in that the first and second annular inserts are in the form of a flat ring on one side, each flat ring having a circular arch of the circumference of a central opening of each annular insert, each circular arch in the form of the letter "C", whereby each rim of a central opening of each serrated segment extends the distance of the annular insert in which a through a hole is provided which houses the shaft and wherein the height of the serrated segment is greater than the height of the arched segment.

4. Divider according to claim 2, characterized in that the annular inserts are made of plastic, while other structural elements are made of steel, primarily of stainless steel.

5. A divider according to claim 1, characterized in that the gear train is mounted through shafts in a housing on which a middle arm is fixedly placed, the middle arm having a distal portion distal to the housing, which, viewed from above, has a rectangular shape, extending to a proximal portion and proximal end thereto the proximal portion in the form of an equilateral triangle, while each of the arms have the form of a flat ring on the opposite sides of which the shorter part (a) of the arm and the longer part (b) of the arm extend to the outside, at which the parts (a, b) of the arms, viewed from above, have a rectangular shape, while their ends have the shape of an equilateral triangle.

\* \* \* \* \*